(12) United States Patent
Kim

(10) Patent No.: US 11,771,782 B2
(45) Date of Patent: Oct. 3, 2023

(54) UV-C LED DISINFECTION DEVICE

(71) Applicant: Gerald Ho Kim, Ontario, CA (US)

(72) Inventor: Gerald Ho Kim, Ontario, CA (US)

( * ) Notice: Subject to any disclaimer, the term of this patent is extended or adjusted under 35 U.S.C. 154(b) by 312 days.

(21) Appl. No.: 17/023,294

(22) Filed: Sep. 16, 2020

(65) Prior Publication Data
US 2021/0085812 A1     Mar. 25, 2021

Related U.S. Application Data

(60) Provisional application No. 62/903,597, filed on Sep. 20, 2019.

(51) Int. Cl.
*A61L 2/10*     (2006.01)
*A61L 2/26*     (2006.01)
*A61L 2/24*     (2006.01)

(52) U.S. Cl.
CPC .................. *A61L 2/10* (2013.01); *A61L 2/24* (2013.01); *A61L 2/26* (2013.01); *A61L 2202/11* (2013.01); *A61L 2202/121* (2013.01); *A61L 2202/122* (2013.01); *A61L 2202/14* (2013.01)

(58) Field of Classification Search
CPC ..... A61L 2/10; A61L 2/24; A61L 2/26; A61L 2202/11; A61L 2202/121; A61L 2202/122; A61L 2202/14; A61L 9/20; A61L 2202/16; A61L 2202/23; A61L 2209/16; C02F 2201/3222; C02F 2201/326; C02F 1/325; C02F 2201/3224
See application file for complete search history.

(56) References Cited

U.S. PATENT DOCUMENTS

| | | | |
|---|---|---|---|
| 2016/0271280 A1* | 9/2016 | Liao | G06F 3/0393 |
| 2020/0338220 A1* | 10/2020 | Kim | B60H 1/00814 |
| 2021/0122667 A1* | 4/2021 | Westerhoff | G02B 6/001 |
| 2021/0244840 A1* | 8/2021 | Mermel | A61B 1/121 |

* cited by examiner

*Primary Examiner* — Regina M Yoo
(74) *Attorney, Agent, or Firm* — Han IP PLLC; Andy M. Han

(57) ABSTRACT

An ultraviolet C (UV-C) disinfection device includes a UV-C light-emitting diode (LED) illuminator which includes a UV-C source module and a UV-C LED coupling module. The UV-C source module includes a heat spreader and a UV LED chip that is mounted on the heat spreader which is configured to be mounted on a printed circuit board (PCB). The UV-C LED coupling module includes a holder and a rod configured to carry a UV-C light emitted from the UV-C LED chip from a first distal end of the rod to an opposite second distal end of the rod such that the UV-C light gets leaks out from a side of the rod to deliver at least a portion of the UV-C light to a surrounding of the rod, with the rod secured with the holder positioning the rod onto the UV-C chip.

9 Claims, 7 Drawing Sheets

DETAIL A

UV-C LED DISINFECTION DEVICE

CROSS REFERENCE TO RELATED PATENT APPLICATION(S)

The present disclosure is part of a non-provisional application claiming the priority benefit of U.S. Patent Application No. 62/903,597, filed 20 Sep. 2019, the content of which being incorporated by reference in its entirety.

TECHNICAL FIELD

The present disclosure generally relates to disinfection devices and, more particularly, to an ultraviolet C (UV-C) light-emitting diode (LED) disinfection device.

BACKGROUND

Unless otherwise indicated herein, the approaches described in this section are not prior art to the claims in this application and are not admitted as prior art by inclusion in this section.

There have been many designs of using UV-C LED to disinfect water in a container or any container. The UV-C light can transmit through most of clear liquid such as water; however, the UV-C light gets absorbed as the light propagate through the liquid. In the case of non-clear water such as juice, milk or microorganism contaminated water can attenuate the propagation of UV-C light very fast. There is a need to develop or improve the delivery of UV-C light to the liquid uniformly.

SUMMARY

The following summary is illustrative only and is not intended to be limiting in any way. That is, the following summary is provided to introduce concepts relating to a heat sink for thermal management in an electronic apparatus. Select embodiments of the novel and non-obvious technique are further described below in the detailed description. Thus, the following summary is not intended to identify essential features of the claimed subject matter, nor is it intended for use in determining the scope of the claimed subject matter.

The present disclosure proposes various designs, concepts, schemes and techniques pertaining to a device to disinfect a large volume of liquid or area uniformly by distributing a UV-C LED emitter.

BRIEF DESCRIPTION OF THE DRAWINGS

The accompanying drawings are included to provide a further understanding of the disclosure and are incorporated in and constitute a part of the present disclosure. The drawings illustrate embodiments of the disclosure and, together with the description, serve to explain the principles of the disclosure. It is appreciable that the drawings are not necessarily in scale as some components may be shown to be out of proportion than the size in actual implementation in order to clearly illustrate the concept of the present disclosure.

DETAILED DESCRIPTION OF PREFERRED EMBODIMENTS

Overview

Figure 1:
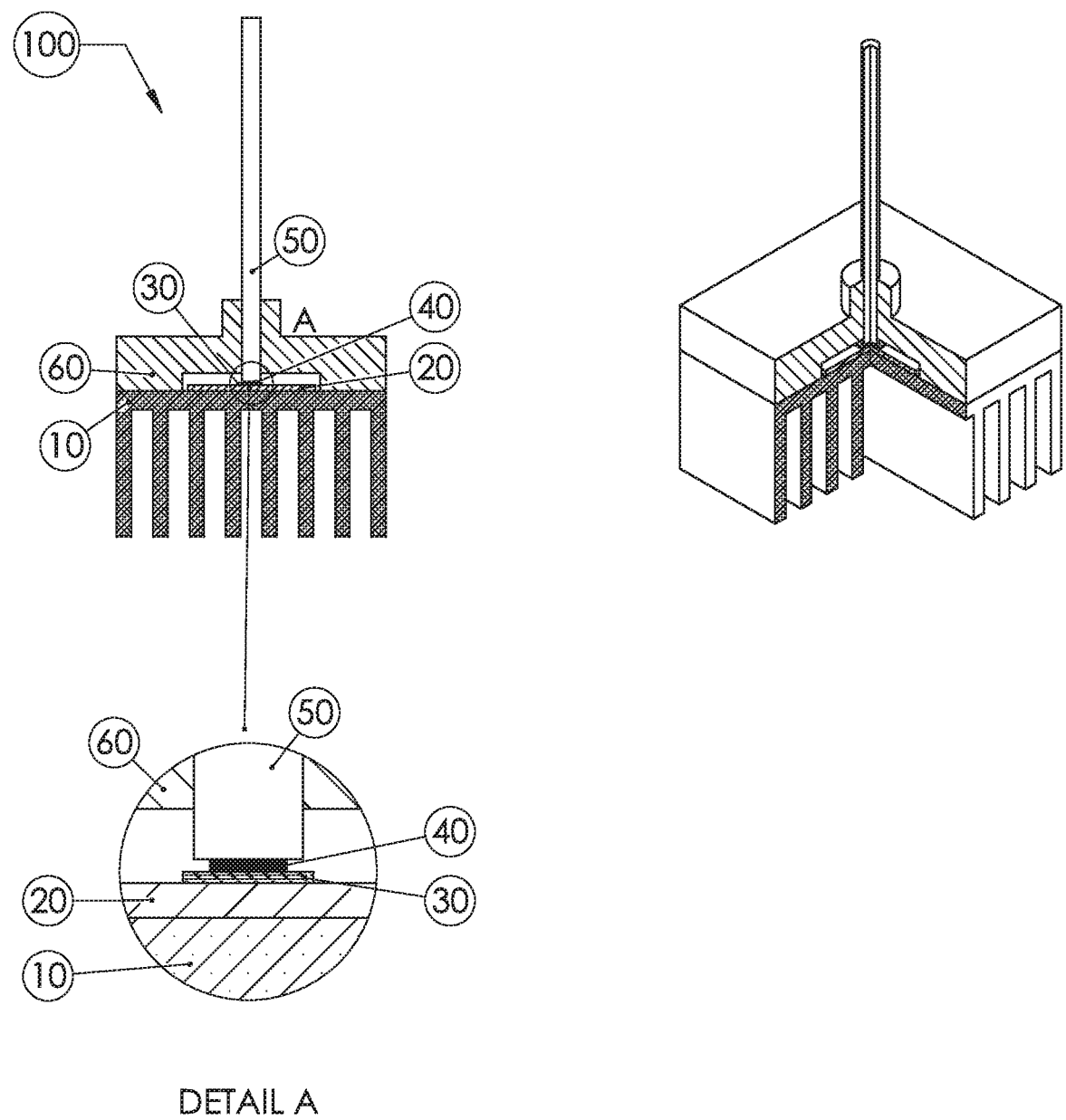
FIG. 1 is a diagram of a basic structure of an example UV-C LED illuminator in accordance with an embodiment of the present disclosure.

The uniform delivery of UV-C light is critical to disinfect the volume of liquid that is contaminated. The present disclosure is focused on a device that deliver UV-C LED light into any liquid uniformly by coupling the UV-C light into a glass rod that transmit UV-C light.

In the case of any contaminated water such as algae or recycled water can have many micro-organisms to prevent the UV-C light to be deeply penetrated. UV-C light will be attenuated as it propagates into the contaminated water. The contamination can be any micro-organisms or non-organic materials. In order to expose uniformly in the contaminated medium, it requires a special apparatus to deliver UV-C light into the medium such as a quartz or sapphire rod that transmit UV-C light.

Designing UV-C light illuminator is very different than any visual light or even other UV LED light. Most of visual or UV light from a LED can be easily coupled into any plastic or glass rod without any trouble. However, UV-C light requires special material such as quartz or sapphire. Most of the material absorbs UV-C light so that designing this kind of device is not practical and a lot of UV-C light will heat up the rod or disintegrate the material.

Most of UV-C disinfection device used in current market uses UV-C light to be directly shine into a liquid medium and the UV-C light can be very effectively disinfect the surface layers of the liquid medium. However, the UV-C light will be attenuated from the surface into the volume of the liquid medium. In order to disinfect the volume of the liquid, the liquid medium must be stirred. A proposed scheme in accordance with the present disclosure uses a UV-C transmitting rod such as quartz or sapphire glass to deliver the UV-C light into the liquid medium without any other mixing or stirring and spread the UV-C light into the liquid medium uniformly to disinfect. The rod is allowing to transfer the UV-C light into the center of the liquid medium to illuminate uniformly the surrounding of the liquid. Without the rod delivering mechanism, it is not possible to illuminate all the liquid medium to disinfect uniformly by the UV-C light.

A critical factor of UV-C LED illuminator is to disinfect a certain volume of liquid such as water, contaminated water, reclaimed water, coffee, tea or milk to deliver a right amount of UV-C energy. Therefore, the UV-C light intensity and on-time duration are very important to disinfect a predetermined disinfection effectiveness such as more than 99% or better. One way to ensure a constant light intensity of the UV-C LED illuminator is to monitor the power level in real-time. A proposed scheme in accordance with the present disclosure includes on a method of placing a photosensor at the end of the light guiding rod to monitor the UV-C light intensity by increasing an injected current into the UV-C LED. A self-closed loop system between UV-C LED, photodetector and a signal process unit are maintained a constant UV-C light intensity for an effectiveness of consistent disinfection.

The UV-C light from the UV-C LED source module is coupled into the end of the rod of the UV-C LED coupling module where the UV-C light is propagated to the other side of the rod without any significant loss in the inside of the rod. If the rod has a relatively high absorption of the UV-C light, then it will not deliver enough UV-C light to the liquid. The absorbed UV-C light becomes a heat into the liquid. It is important to transmit UV-C light without any absorption in the rod. A quartz and sapphire rod are cost material to use for disinfection device.

The UV-C LED coupling module is combined with a container that filled with a liquid where the length of the rod is cut into a proper size so that the UV-C light coupled into the rod emits from the side and the other end of the rod illuminating the inside of the container by closely equal UV-C light intensity for uniform disinfection. The length and diameter of the rod is precisely designed to deliver the UV-C light into the container. The rod diameter is important factor to determine the coupling efficiency between the rod and the UV-C LED, and the rod length is also allowing to deliver uniform UV-C light into the liquid. If the length of the rod is relatively short, then the bottom of the container is not getting enough UV-C light for disinfection. Also, the rod diameter is too small then the UV-C coupling efficiency will be reduced. A proper rod diameter and length are needed to illuminate uniformly inside of the container.

One of advantage of UV-C LED based disinfection system with the rod design is to deliver high power of UV-C light into heavily contaminated water or other liquid. Current design of shining UV-C light from UV-C LED or UV-C mercury lamp directly into the liquid has limitation of penetrating into the liquid uniformly. A proposed scheme in accordance with the present disclosure allows penetrating into the liquid without attenuating of UV-C light at the surface and deliver the UV-C light into the liquid medium effectively. The UV-C mercury lamps in a low and medium pressure are used in many municipal water disinfection systems and advanced oxidation process (AOP) of reclaimed water, but the mercury lamp is directly insert into water-flow to disinfect or generate more radical oxygen for disinfection. The mercury lamp has an issue of directly inserting the low or medium pressure of mercury lamp into contaminated water and the mercury lamp can contaminated the water if the lamp is broken or the mercury gas is leak into the water. A proposed scheme in accordance with the present disclosure eliminates the potential danger of breaking the mercury lamp to contaminate the water since the rod doesn't carry any mercury vapor. The proposed scheme adds no mercury contamination due to breakage of the UV-C illuminator and safe to use in any liquid disinfection application.

The application of UV-C LED disinfection device is using in automobile HVAC system disinfection, fish aquarium water disinfection, potable water container disinfection, water reservoir disinfection, swimming pool disinfection and any reclaim water disinfection. Also, the UV-C disinfection device that uses a UV-C transmitting (>90% of transmission). This device can be used as a portable disinfection unit for hospital, household, hotel, restaurant, public bathroom and many other places.

Illustrative Implementations

FIG. 1 shows a basic structure of UV-C LED illuminator (100) that combined with a UV-C LED source module and a UV-C LED coupling module is shown in FIG. 1. A rod (50) is coupled onto a UV-C chip (40) using a holder (60). The rod can be a quartz or sapphire material to transmit UV-C light for disinfection. The rod is mounted on the holder (60) to securely mount the rod (50) in place for coupling the LED light. Due to high thermal dissipation for UV-C LED, specially a low light coupling efficiency of the UV-C LED, the UV-C chip (40) is mounted on a heat spreader (30) where the substrate (30) can be a high thermal conducting material such as a non-metal structure of ceramic, diamond, silicon carbide, or silicon. The heat spreader (30) is mounted on a PCB (20) where the PCB can be a metal PCB or fiber-glass PCB. The PCB (20) is also mounted on a heatsink (10) for final heat dissipation into air.

Figure 2:
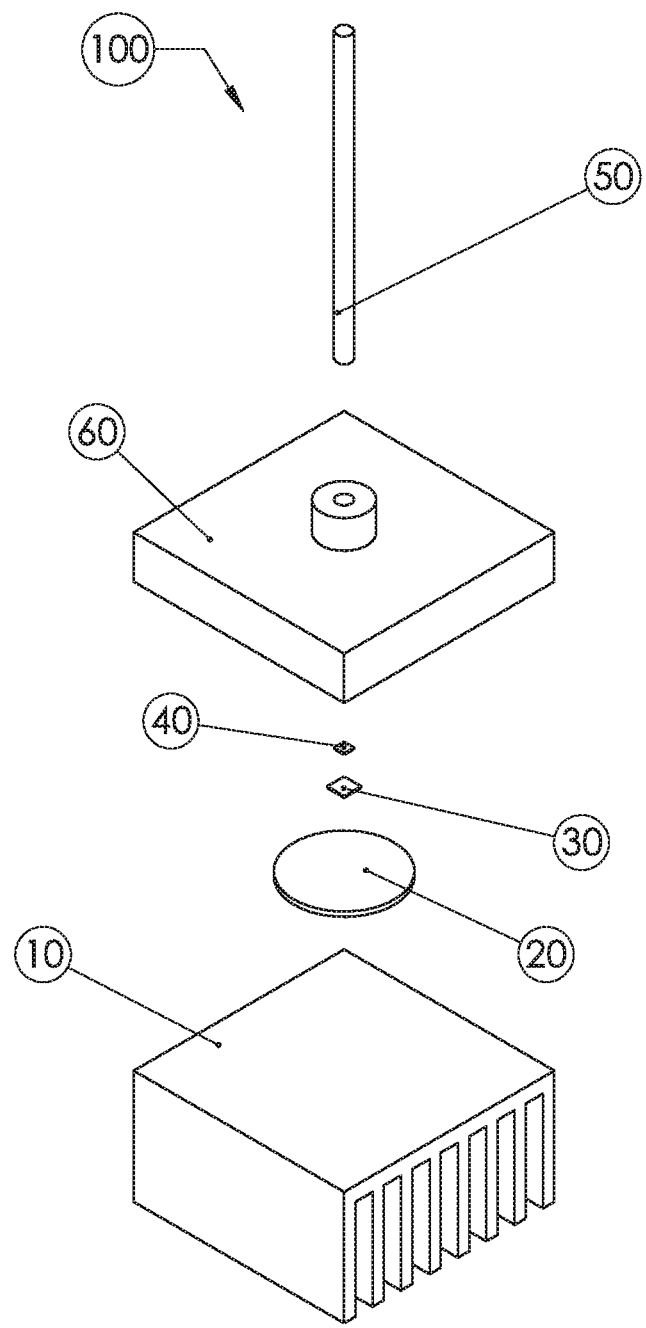
FIG. 2 is a diagram of an exploded view of the UV-C LED illuminator of FIG. 1.

FIG. 2 shows an explored view of the UV-C LED illuminator (100). The UV-C LED illuminator (100) consists of a heatsink (10), PCB (20), substrate (30), UV-C chip (40), holder (60), and rod (50). The UV-C chip, the substrate (30) and the PCB (20) are bonded to transfer a maximum heat to the heatsink (10). Depending on the thermal dissipation requirement of the UV-C LED source module the heatsink (10) may require a fan to dissipate a large heat loading.

Figure 3:
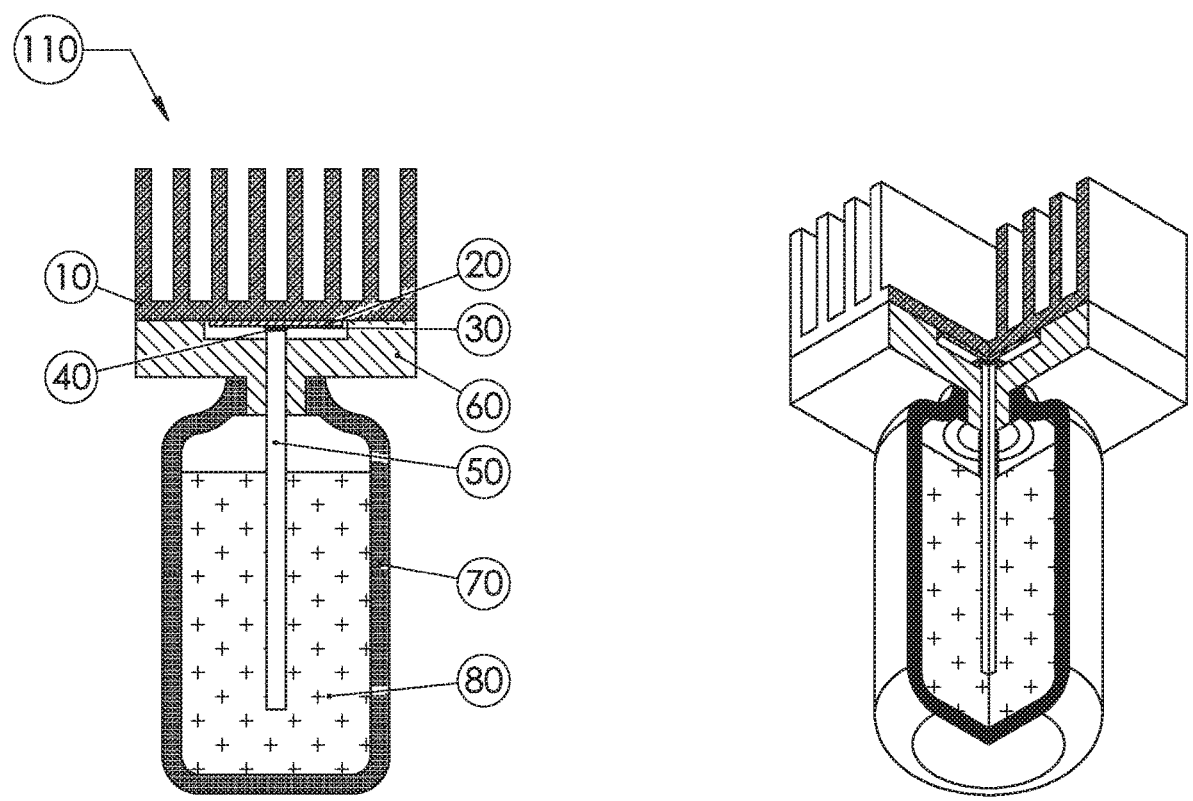
FIG. 3 is a diagram of an example application of the UV-C LED illuminator of FIG. 1.

FIG. 3 shows an application of the UV-C LED illuminator (100) is placed on a container (70) where liquid (80) is filled to make an UV-C disinfection device (110). The UV-C disinfection device (110) demonstrates the UV-C LED illuminator (100) is uniformly illuminating UV-C light into the container (70) filled with the liquid (80). The rod (50) is placed in the liquid (80) deep enough to create uniform illumination inside of the container (80). This will allow to deliver UV-C light into the liquid (80) uniformly. It is very important to deliver uniform dosage of UV-C light into the liquid (80) in order to disinfect 99% or better disinfection in the liquid (80) that is filled in the container (70).

Figure 4:
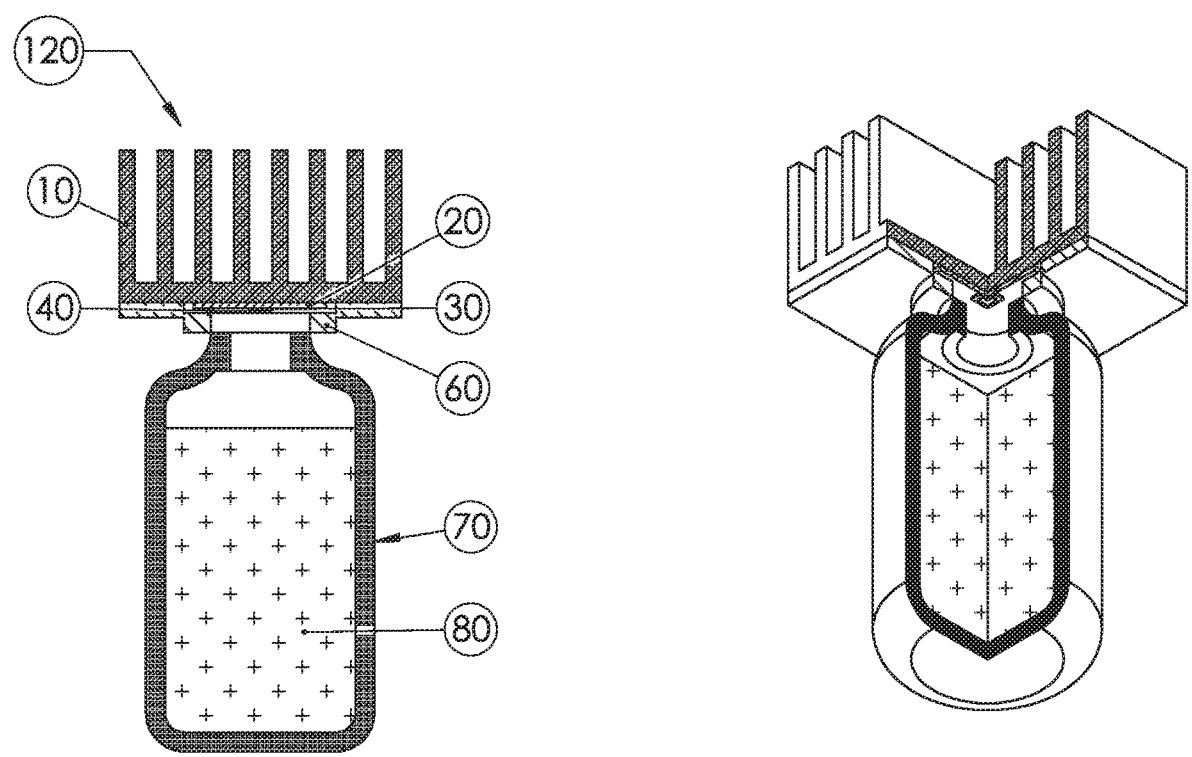
FIG. 4 is a diagram of an example UV-C LED disinfection device in accordance with an embodiment of the present disclosure.

FIG. 4 shows a typical UV-C LED disinfection device (120) that is mounted on a container (70) for disinfection. The UV-C LED is placed on the top of the container (70) and UV-C light is exposed on the top of the liquid (80). The UV-C light will penetrate the liquid (80) from the top-surface to the bottom. If the liquid (80) is not highly transmitting the UV-C light, the light intensity of the UV-C light will be attenuated as it propagates through the liquid (80). In this case, the disinfection effectiveness will be degraded due to a lack of the UV-C light. This invention overcome the issue of UV-C light attenuation caused by the liquid (80) absorption and disinfect the liquid (80) uniformly. The UV-C LED disinfection device (120) is a typical setup of UV-C light illumination application in current market.

Figure 5A:
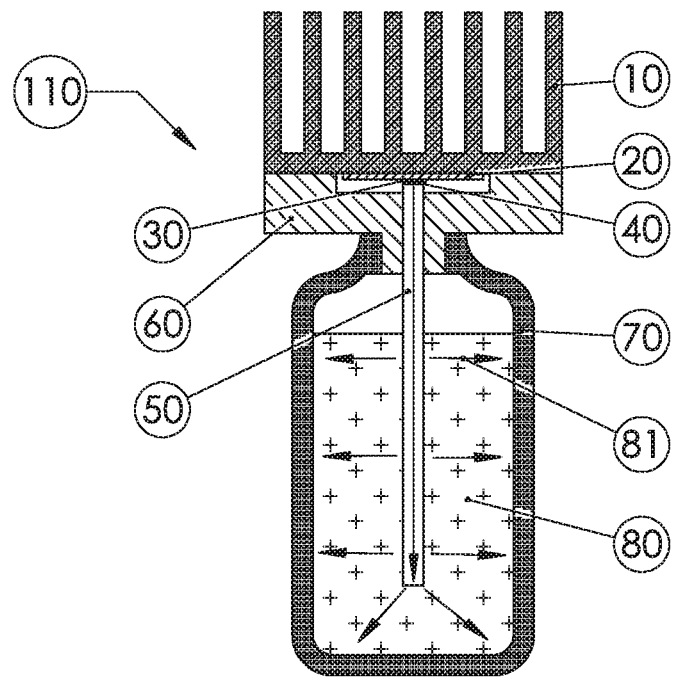
FIG. 5A is a diagram of an example scenario of uniformly illuminating a liquid inside a container in accordance with an embodiment of the present disclosure.

FIG. 5A shows an illustration of uniformly illuminating the liquid (80) inside of the container (70). The UV-C chip (40) is emitting a disinfection wavelength of 100 nm to 280 nm. The rod (50) transmits more than 90% of UV-C light into the liquid (80). As the UV-C light enters the rod (50), the UV-C light will be leak through its surface to the liquid (80). However, the rod (50) will carry the UV-C light down to the bottom of the container (70) without a lot of loss other than leaking through the surface of the rod (50) by Fresnel's reflection loss. This will deliver a uniform UV-C light intensity into the liquid (80). The light rays (81) illustrates a distribution of UV-C light through the rod (50) and the UV-C light is reaching uniformly in the container (70)

Figure 5B:
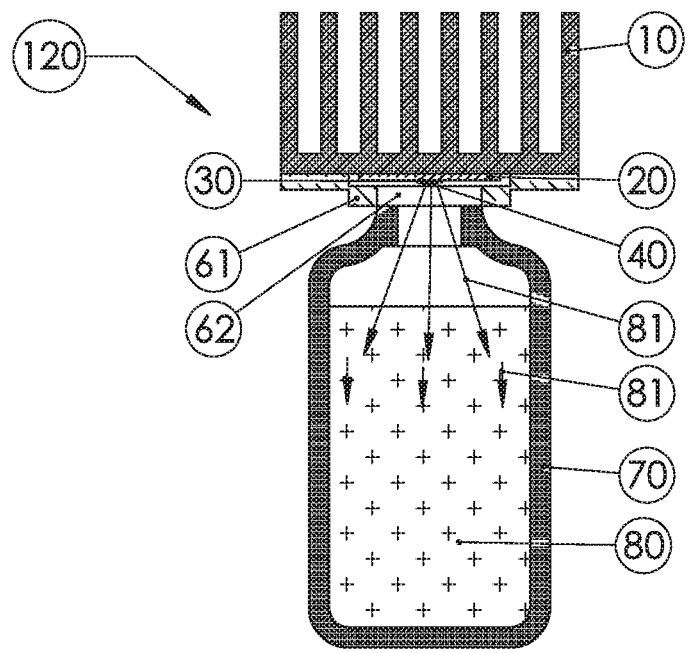
FIG. 5B is a diagram of an example scenario of an example UV-C light shining on a liquid in accordance with an embodiment of the present disclosure.

FIG. 5B shows an illustration of a typical UV-C light shining on the liquid (80) where the light rays (81) propagate through a window (62) and window mount (61). The light rays (81) get attenuated as it propagates into the liquid (80). Due to the attenuation of the light rays (81), the effectiveness of disinfection from the top of the liquid (80) to the bottom of the container (70) will be different. The top of the liquid (80) will get a high disinfection effect compare to the bottom side of the liquid (80) since the most UV-C light intensity will be absorbed at the surface of the liquid (80).

Figure 6:
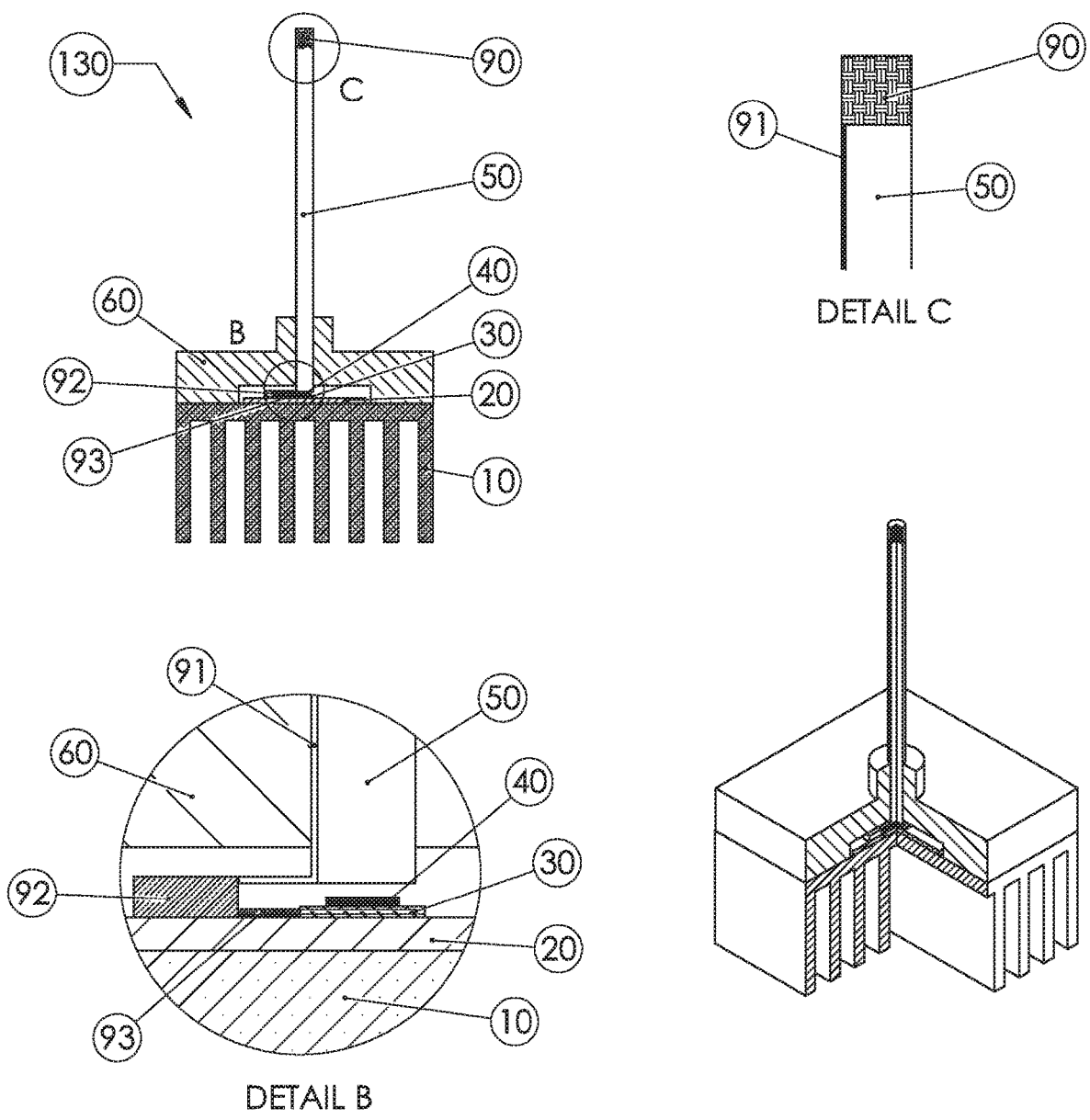
FIG. 6 is a diagram of an example application of the UV-C LED illuminator of FIG. 1 with a photo sensor.

FIG. 6 shows a drawing of the LED illuminator (100) with a photo sensor (90) attached to the end of the rod (50) electrically connected by a wire (91). The wire (91) is connected to the photo sensor (90) and a signal process unit (92) to measure the light intensity of the UV-C chip, and the UV-C light intensity is maintained at a constant level. Due to a constant and uniform disinfection of germs, the light intensity of UV-C illuminator is controlled by a closed-loop feedback system to maintain a constant level of UV-C illumination intensity. It is important to maintain the constant level of UV-C light intensity; otherwise, the UV-C disinfection device (110) will not work effectively.

Figure 7:
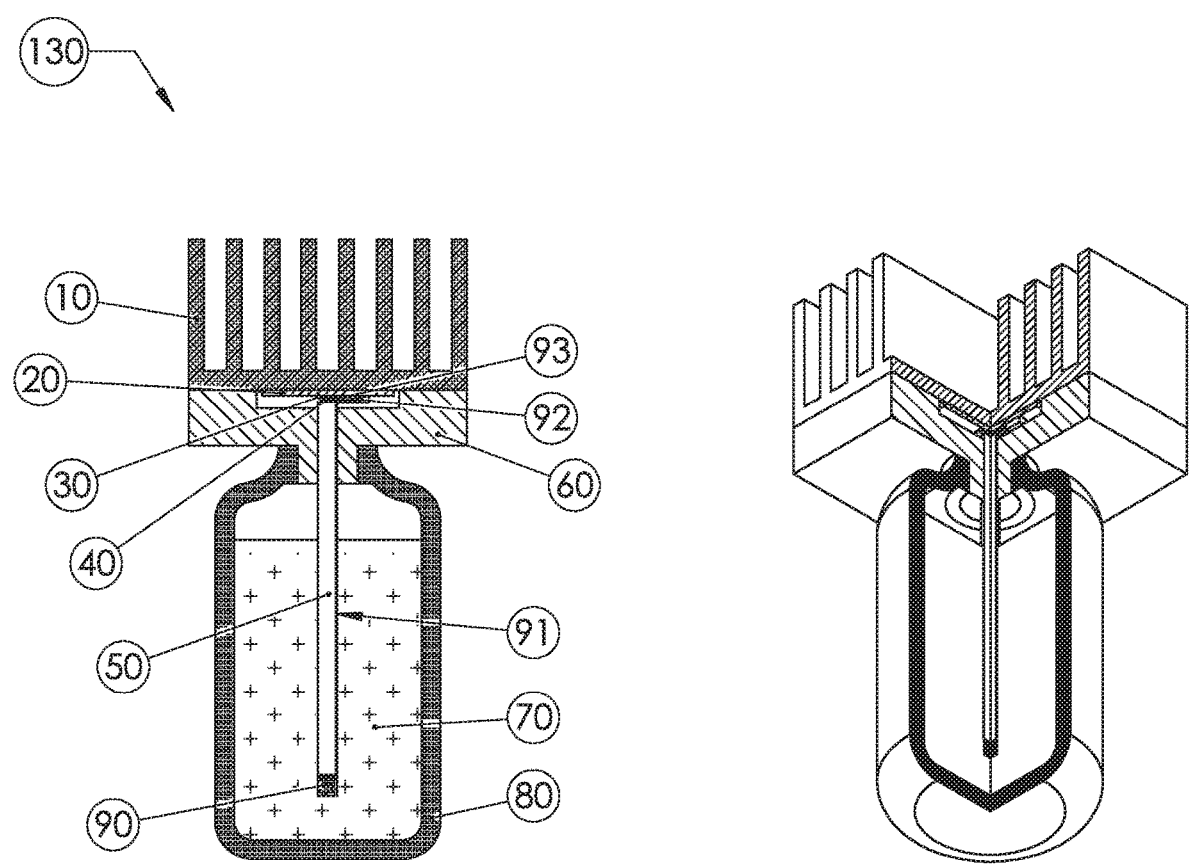
FIG. 7 is a diagram of an example UV-C LED disinfection device with a photo sensor in accordance with an embodiment of the present disclosure.

FIG. 7 shows a UV-C disinfection device (130) that is mounted on the container (70) along with a photo sensor (90). The device (130) provide a constant UV-C light intensity and deliver a uniform disinfection effectiveness.

In view of the above description, those with ordinary skills in the art would appreciate that one main point of various implementations of the present disclosure is getting the UV-C transmitting quartz rod to leak all UV-C light into the liquid due to small change in the index of refraction between the quartz rod and the liquid (e.g., water or a different liquid) than the rod and air. For instance, if the quartz rod (index of refraction 1.46) is placed in water (index of refraction 1.33), a significant amount of UV-C light would be emitted out from the side of the quartz rod and into the water. If the liquid has an index of refraction close to 1.46, then there would be no critical angle at a boundary of the interface. The key is that, in case that the index of refraction of the liquid is close to the index of refraction of the quartz, a majority of UV-C light would be emitted out from the quartz and enter into the liquid. In the case of sapphire rod (index of refraction 1.76), the index of refraction of the liquid would need to be around 1.76 and a minimum amount of UV-C light would be emitted out at the side of the sapphire rod while a majority of the UV-C light would be emitted out at the end of the rod. In an event that the sapphire rod is placed in water, then the difference of the index of refraction would 0.43 (=1.76−1.33), and accordingly a majority of UV-C light would not be emitted out from the side of the rod into the water. In such a case the rod would act like a waveguide (e.g., with total internal refraction). Therefore, ideally, the difference in the index of refraction between the rod and the liquid should be minimized. For instance, the difference in the index of refraction may be between 0.05 to 0.43. This requirement may cover the case of a quartz rod (1.43) being placed in water (1.33), and also the case of a sapphire rod (1.76) being placed in water (1.33).

Highlight of Select Features

In view of the above, select features in accordance with the present disclosure are highlighted below.

In one aspect, a UV-C disinfection device may include a UV-C LED illuminator which may include a UV-C source module and a UV-C LED coupling module. The UV-C source module may include a heat spreader and a UV LED chip that is mounted on the heat spreader which is configured to be mounted on a printed circuit board (PCB). The UV-C LED coupling module may include a holder and a rod configured to carry a UV-C light emitted from the UV-C LED chip from a first distal end of the rod to an opposite second distal end of the rod such that the UV-C light gets leaks out from a side of the rod to deliver at least a portion of the UV-C light to a surrounding of the rod, with the rod secured with the holder positioning the rod onto the UV-C chip.

In some implementations, the UV-C disinfection device may also include a container. In such cases, the UV-C LED coupling module and the UV-C source module may be mounted on the container where the rod is inserted into the container to illuminate an interior of the container uniformly. In some implementations, a length of the rod may be such that a uniform illumination is provided inside the container where a liquid to be disinfected is held. In some implementations, a difference between an index of refraction of the rod and an index of refraction of the liquid is in a range between 0.05 and 0.43.

In some implementations, the rod may be made of UV-C transmitting sapphire glass. Alternatively, the rod may be made of UV-C transmitting quartz glass.

In some implementations, emission of the UV-C light from the rod may be greater than or equal to 90 percent.

In some implementations, an index of refraction of the rod may be greater than or equal to 1.3 and less than 2.5.

In one aspect, a UV-C disinfection device may include a UV-C LED illuminator which may include a UV-C source module, a UV-C LED coupling module and a UV-C sensor module. The UV-C source module may include a heat spreader and a UV LED chip that is mounted on the heat spreader which is configured to be mounted on a PCB. The UV-C LED coupling module may include a holder and a rod configured to carry a UV-C light emitted from the UV-C LED chip from a first distal end of the rod to an opposite second distal end of the rod such that the UV-C light gets leaks out from a side of the rod to deliver at least a portion of the UV-C light to a surrounding of the rod, with the rod secured with the holder positioning the rod onto the UV-C chip. The UV-C sensor module may include a photo sensor and a signal processing unit. The photo sensor may be mounted at the first distal end of the rod opposite to the UV-C chip, and the photo sensor may be configured to monitor a light intensity of the UV-C light. The signal processing unit may be configured to receive light intensity information from the photo sensor and to adjust an output power of the UV-C chip to maintain a constant lever of the light intensity of the UV-C light.

In some implementations, the UV-C disinfection device may also include a container. In such cases, the UV-C LED coupling module and the UV-C source module may be mounted on the container where the rod is inserted into the container to illuminate an interior of the container uniformly. In some implementations, a length of the rod may be such that a uniform illumination is provided inside the container where a liquid to be disinfected is held. In some implementations, a difference between an index of refraction of the rod and an index of refraction of the liquid is in a range between 0.05 and 0.43.

In some implementations, the rod may be made of UV-C transmitting sapphire glass. Alternatively, the rod may be made of UV-C transmitting quartz glass.

In some implementations, emission of the UV-C light from the rod may be greater than or equal to 90 percent.

In some implementations, an index of refraction of the rod may be greater than or equal to 1.3 and less than 2.5.

In some implementations, the photo sensor, the signal processing unit, and the UV-C LED chip may form a closed-loop system to maintain a uniformity in the light intensity of the UV-C light.

ADDITIONAL NOTES AND CONCLUSION

The herein-described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Further, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An ultraviolet C (UV-C) disinfection device, comprising:
   a UV-C light-emitting diode (LED) illuminator comprising:
      a UV-C LED source module comprising:
         a heat spreader; and
         a UV-C LED chip that is mounted on the heat spreader which is configured to be mounted on a printed circuit board (PCB);
      a UV-C LED coupling module comprising:
         a holder; and
         a rod configured to carry a UV-C light emitted from the UV-C LED chip from a first distal end of the rod to an opposite second distal end of the rod such that the UV-C light gets leaks out from a side of the rod to deliver at least a portion of the UV-C light to a surrounding of the rod, with the rod secured with the holder positioning the rod onto the UV-C LED chip; and
      a UV-C sensor module comprising:
         a photo sensor mounted at the first distal end of the rod opposite to the UV-C LED chip, the photo sensor configured to monitor a light intensity of the UV-C light; and
         a signal processing unit configured to receive light intensity information from the photo sensor and to adjust an output power of the UV-C LED chip to maintain a constant level of the light intensity of the UV-C light.

2. The UV-C disinfection device of claim 1, further comprising:
   a container,
   wherein the UV-C LED coupling module and the UV-C source module are mounted on the container where the rod is inserted into the container to illuminate an interior of the container uniformly.

3. The UV-C disinfection device of claim 2, wherein a length of the rod is such that a uniform illumination is provided inside the container where a liquid to be disinfected is held.

4. The UV-C disinfection device of claim 3, wherein a difference between an index of refraction of the rod and an index of refraction of the liquid is in a range between 0.05 and 0.43.

5. The UV-C disinfection device of claim 1, wherein the rod is made of UV-C transmitting sapphire glass.

6. The UV-C disinfection device of claim 1, wherein the rod is made of UV-C transmitting quartz glass.

7. The UV-C disinfection device of claim 1, wherein emission of the UV-C light from the rod is greater than or equal to 90 percent.

8. The UV-C disinfection device of claim 1, wherein an index of refraction of the rod is greater than or equal to 1.3 and less than 2.5.

9. The UV-C disinfection device of claim 1, wherein the photo sensor, the signal processing unit, and the UV-C LED chip form a closed-loop system to maintain a uniformity in the light intensity of the UV-C light.

* * * * *